United States Patent
Ju et al.

(10) Patent No.: US 11,066,316 B2
(45) Date of Patent: Jul. 20, 2021

(54) TREATMENT OF OIL AND GREASE IN WATER USING ALGAE

(71) Applicants: Lu-Kwang Ju, Akron, OH (US); Majid Hosseini, Cuyahoga Falls, OH (US)

(72) Inventors: Lu-Kwang Ju, Akron, OH (US); Majid Hosseini, Cuyahoga Falls, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 14/909,522

(22) PCT Filed: Aug. 1, 2014

(86) PCT No.: PCT/US2014/049433
§ 371 (c)(1),
(2) Date: Feb. 2, 2016

(87) PCT Pub. No.: WO2015/017794
PCT Pub. Date: Feb. 5, 2015

(65) Prior Publication Data
US 2016/0167995 A1    Jun. 16, 2016

Related U.S. Application Data

(60) Provisional application No. 61/861,511, filed on Aug. 2, 2013.

(51) Int. Cl.
| | |
|---|---|
| C12N 1/12 | (2006.01) |
| C02F 3/32 | (2006.01) |
| C02F 3/00 | (2006.01) |
| C02F 101/32 | (2006.01) |
| C02F 103/10 | (2006.01) |
| C02F 103/32 | (2006.01) |
| C02F 101/30 | (2006.01) |

(52) U.S. Cl.
CPC .............. *C02F 3/322* (2013.01); *C02F 3/006* (2013.01); *C12N 1/12* (2013.01); *C02F 2101/301* (2013.01); *C02F 2101/32* (2013.01); *C02F 2103/10* (2013.01); *C02F 2103/32* (2013.01); *C02F 2103/322* (2013.01); *C02F 2209/001* (2013.01); *C02F 2209/02* (2013.01); *C02F 2209/06* (2013.01); *C02F 2209/22* (2013.01)

(58) Field of Classification Search
None
See application file for complete search history.

(56) References Cited

U.S. PATENT DOCUMENTS

| | | | | |
|---|---|---|---|---|
| 5,372,943 | A | * | 12/1994 | Inlow .................... C07K 14/53 |
| | | | | 428/402.2 |
| 2009/0220304 | A1 | | 9/2009 | Ballew et al. |
| 2010/0210002 | A1 | * | 8/2010 | McCaffrey ............. A01G 33/00 |
| | | | | 435/257.1 |
| 2010/0297714 | A1 | | 11/2010 | Ju |
| 2013/0115664 | A1 | | 4/2013 | Khanna et al. |

FOREIGN PATENT DOCUMENTS

| | | |
|---|---|---|
| EP | 2546352 A1 | 1/2013 |
| JP | 2003102467 A | 3/2003 |
| WO | 2012040698 A2 | 3/2012 |

OTHER PUBLICATIONS

Magat W. J. "Metabolism of cyclopropane fatty acids by Ochromonas danica". 1970. Iowa State University, digital repository. Retrospective Theses and Dissertations. Paper 4182, pp. 1-109.*

Mooney et al. "Direct incorporation of fatty acids into halosulfatides of Ochromonas danica". Biochemistry, 1972, vol. 11, No. 25, pp. 4839-4844.*

Pringsheim. "On the Nutrition of Och~omonas." Quarterly Journal of Microscopical Science [online], Mar. 1952 [Retrieved on Jun. 10, 2014], vol. 93, Part 1, Retrieved from the Internet: <URL: http:/{jcs.biologists.org/content/s3-93/21/71.full.pdf>, pp. 71-96, p. 71, para 2; p. 77, para 3.

* cited by examiner

*Primary Examiner* — Vera Afremova
(74) *Attorney, Agent, or Firm* — Renner Kenner Greive Bobak Taylor & Weber

(57) ABSTRACT

A method for treating an oil-containing medium including oil or grease or both oil and grease includes the steps of combining algae with an oil-containing medium and allowing the algae to engulf or uptake at least a portion of the oil or grease in the oil-containing medium. A mixture for treating oil or grease or both oil and grease includes an oil-containing medium including oil or grease or both oil and grease and phagotrophic algae that engulf or uptake at least a portion of the oil or grease in the oil-containing medium.

20 Claims, No Drawings

TREATMENT OF OIL AND GREASE IN WATER USING ALGAE

CROSS-REFERENCE TO RELATED APPLICATION

This application claims priority to U.S. Provisional Patent Application No. 61/861,511 filed on Aug. 2, 2013, the contents of which are incorporated herein by reference.

FIELD OF THE INVENTION

The present invention generally relates to treating water having oils and greases therein. The present invention further relates to the use of phagotrophic algae to engulf and process oils and greases that can be found in water and wastewater.

BACKGROUND OF THE INVENTION

Oils and greases present in water and wastewater may contain a broad range of chemicals and minerals, and may be from different animal or plant origins. In wastewater the oily substances can be dissolved, emulsified, or suspended within the water. These oils can also form floating masses on the water surface and can be suspended or form sediments within the bulk water phase. The oil concentration in some industrial wastewaters is as high as 40 g/L.

There are known microorganisms that can consume dissolved oil molecules but the ability of these microorganisms to degrade the oil depends on the oil components and concentrations. Oils that are not readily biodegraded are harmful, and even toxic, to the environment. Even worse, the oil in wastewater usually appears in an emulsion form with small droplets, making them hard to collect by physical methods. The insolubility also makes them more resistant to biodegradation.

Industrial wastewater from chemical plants and oil refineries is particularly difficult to treat, as it can contain large amounts of oils and chemicals (e.g. phenolic compounds). These oils and chemicals are potentially toxic to environment and hard to degrade.

Known methods of treating oily water and wastewaters include coagulation, electro-coagulation, electro-floatation, flocculation with electro-floatation, air floatation, adsorption, membrane bioreactors, ultra filtration, and ozone. However, these methods can be expensive, can sometimes be impractical on a large scale, or can be incapable of removing large quantities of oil from the water.

Thus, there is a need in the art for an improved method and system for removing or processing oil and grease from water. There is a further need for an improved method and system that is environmentally friendly and is capable of removing various forms (e.g. dissolved, emulsified, and free) of oils, other hydrocarbon-derived compounds, and phenolic compounds present in oily waste and wastewater.

SUMMARY OF THE INVENTION

In a first embodiment, the present invention provides a method for treating an oil-containing medium including oil or grease or both oil and grease, the method comprising the steps of combining algae with an oil-containing medium, and allowing the algae to engulf or uptake at least a portion of the oil or grease in the oil-containing medium.

In a second embodiment, the present invention provides a method as in the first embodiment, wherein the oil-containing medium includes a mineral medium and the method includes growing the algae within the mineral medium.

In a third embodiment, the present invention provides a method as in either the first or second embodiment, wherein the algae are phagotrophic.

In a fourth embodiment, the present invention provides a method as in any of the first through third embodiments, wherein the algae are *Ochromonas danica*.

In a fifth embodiment, the present invention provides a method as in any of the first through fourth embodiments, further comprising the steps of collecting the algae and producing an algal product.

In a sixth embodiment, the present invention provides a method as in any of the first through fifth embodiments, further comprising the step of allowing the algae to grow by engulfing or uptaking at least a portion of the oil in the oil-containing medium.

In a seventh embodiment, the present invention provides a method as in any of the first through sixth embodiments, wherein the mineral medium comprises nitrilotriacetic acid, $KH_2PO_4$, $MgCO_3$, $CaCO_3$, $NH_4Cl$, $MgSO_4 \cdot 7H_2O$, yeast extract, peptone, $Na_2EDTA$, $FeCl_3 \cdot 6H_2O$, $H_3BO_3$, thiamine, biotin, $MnCl_2 \cdot 4H_2O$, $ZnSO_4 \cdot 7H_2O$, $CoCl_2 \cdot 6H_2O$, and $Na_2MoO_4 \cdot 2H_2O$.

In an eighth embodiment, the present invention provides a method as in any of the first through seventh embodiments, wherein the oil-containing medium comprises a surfactant.

In a ninth embodiment, the present invention provides a method as in any of the first through eighth embodiments, wherein the surfactant is polysorbate 80.

In a tenth embodiment, the present invention provides a method as in any of the first through ninth embodiments, wherein the oil-containing medium comprises waste cooking oil.

In an eleventh embodiment, the present invention provides a method as in any of the first through tenth embodiments, further comprising the step of depleting at least one soluble nutrient component essential for microbial growth.

In a twelfth embodiment, the present invention provides a method as in any of the first through eleventh embodiments, further comprising the step of allowing phagotrophic algae to grow as the predominant algae, after the step of depleting at least one soluble nutrient component essential for microbial growth.

In a thirteenth embodiment, the present invention provides a mixture for treating oil or grease or both oil and grease comprising an oil-containing medium including oil or grease or both oil and grease and phagotrophic algae engulfing or uptaking at least a portion of the oil or grease in the oil-containing medium.

In a fourteenth embodiment, the present invention provides a mixture as in the thirteenth embodiment, wherein the algae are *Ochromonas danica*.

In a fifteenth embodiment, the present invention provides a mixture as in either the thirteenth or fourteenth embodiments, wherein the oil-containing medium comprises a mineral medium that contains nutrients essential for the algae to reproduce.

In a sixteenth embodiment, the present invention provides a mixture as in any of the thirteenth through fifteenth embodiments, wherein the mineral medium comprises nitrilotriacetic acid, $KH_2PO_4$, $MgCO_3$, $CaCO_3$, $NH_4Cl$, $MgSO_4 \cdot 7H_2O$, yeast extract, peptone, $Na_2EDTA$, $FeCl_3 \cdot 6H_2O$, $H_3BO_3$, thiamine, biotin, $MnCl_2 \cdot 4H_2O$, $ZnSO_4 \cdot 7H_2O$, $CoCl_2 \cdot 6H_2O$, and $Na_2MoO_4 \cdot 2H_2O$.

In a seventeenth embodiment, the present invention provides a mixture as in any of the thirteenth through sixteenth embodiments, wherein the oil-containing medium comprises a surfactant.

In an eighteenth embodiment, the present invention provides a mixture as in any of the thirteenth through seventeenth embodiments, wherein the surfactant is polysorbate 80.

In a nineteenth embodiment, the present invention provides a mixture as in any of the thirteenth through eighteenth embodiments, wherein the oil-containing medium comprises waste cooking oil.

DETAILED DESCRIPTION OF ILLUSTRATIVE EMBODIMENTS

The present invention generally relates to treating water having oils and greases therein. The present invention further relates to the use of phagotrophic algae to engulf oils and greases that can be found in water and wastewater and subsequently degrading or processing the oils and greases and associated components.

In the present invention, a medium comprises water and at least one oil or at least one grease or both at least one oil and at least one grease. The medium is also described herein as oil-containing water or an oil-containing medium. The oil-containing medium must comprise water as algae need water to survive. An oil-containing medium may comprise other components in addition to the oil and water. As used herein, oil-containing water and oil-containing medium include those instances where the water or medium contains grease, instead of or in addition to the oil. It should be appreciated that these terms "oil-containing water" and "oil-containing medium" refer to any combination of oil or grease or both oil and grease, and water, although embodiments of the invention are particularly useful with oil and/or grease that is microdispersed within the medium.

Useful oils and greases can include waste cooking oil, yellow grease, brown grease, olive oil, soybean oil, palm oil, rapeseed oil, flax seed oil, caster oil, coconut oil, sesame oil, crude oil, petroleum refinery oil, biodiesel, soap stuff, biocrude oil produced from biomass or waste organics by for example hydrothermal, pyrolysis, and fast pyrolysis processes, saturated aliphatic hydrocarbons, unsaturated aliphatic hydrocarbons, aromatic hydrocarbons, cyclic hydrocarbons, any of the above oil and hydrocarbons modified to introduce additional functional groups such as hydroxyl, carboxyl, amine, ester, and ether groups, and any other hydrophobic liquids that are present in water as separate phases and that do not kill the algae on contact, and combinations thereof.

In embodiments where it is desired for the algae to grow or reproduce, oils and greases can provide nutrients essential for the algae to grow or reproduce. In one or more embodiments, essential nutrients can be added to the oil-containing medium. These essential nutrients are those that allow the algae to grow or reproduce and these nutrients are not required in embodiments where it is not desired for the algae to grow or reproduce. In embodiments where it is not desired for the algae to grow or reproduce, the medium is only required to include oil and/or grease and water.

In embodiments where essential nutrients are added, a mineral medium comprises these essential nutrients. In these embodiments, a mineral medium is combined with the water and oil and/or grease. In one or more embodiments, a mineral medium comprises one or more of the following components: nitrilotriacetic acid, $KH_2PO_4$, $MgCO_3$, $CaCO_3$, $NH_4Cl$, $MgSO_4.7H_2O$, yeast extract, peptone, $Na_2EDTA$, $FeCl_3.6H_2O$, $H_3BO_3$, thiamine, biotin, $MnCl_2.4H_2O$, $ZnSO_4.7H_2O$, $CoCl_2.6H_2O$, $Na_2MoO_4.2H_2O$ and glucose.

In one or more embodiments, a mineral medium comprises one or more of the following amounts: 0.2 g/L nitrilotriacetic acid, 0.3 g/L $KH_2PO_4$, 0.4 g/L $MgCO_3$, 0.05 g/L $CaCO_3$, 0.24 g/L $NH_4Cl$, and 0.1 g/L $MgSO_4.7H_2O$ 10 g/L glucose, 0.5 g/L peptone, 0.5 g/L yeast extract, 4.4 mg/L $Na_2EDTA$, 3.15 mg/L $FeCl_3.6H_2O$, 0.97 mg/L $H_3BO_3$, 0.25 mg/L thiamine, 0.18 mg/L $MnCl_2.4H_2O$, 0.02 mg/L $ZnSO_4.7H_2O$, 0.01 mg/L $CoCl_2.6H_2O$, 6 µg/L $Na_2MoO_4.2H_2O$ and 2.5 µg/L biotin. In one or more embodiments, a mineral medium can comprise one or more of the above amounts in an approximation to the amounts given above.

The present invention utilizes algae, particularly those with phagotrophic capability, to treat or process the at least one oil or at least one grease or both at least one oil and at least one grease that is contained within a medium. The phagotrophic algae can engulf droplets and particulates, metabolize the oily compounds, and grow using the oily substrates as a carbon source. Here, grow means that the algae increase in population as a result of engulfing and processing the oil. Evidence suggests that at least some algae species are able to degrade the components in the oil including the harmful phenolics and phenolic mixtures. The use of algae provides an effective method for treating oily wastewater in large scales.

While it is envisioned that phagotrophic algae are particularly useful for the present invention, the algae utilized can also be classified as photosynthetic, heterotrophic, and osmotrophic. The algae can also have more than one of these classifications.

Phagotrophic algae are those that grow by engulfing their food, photosynthetic algae are those that grow by using light as the energy source, heterotrophic algae are those that feed on organic substrates, and osmotrophic algae uptake dissolved compounds through a membrane via osmosis or other active transport mechanisms (excluding phagotrophy) across the membrane.

Phagotrophic algae are algae that feed by engulfing their food, similar to the function of a mouth. Because of this ability to swallow and degrade their food, phagotrophic algae are particularly useful in the present invention. Oils have limited solubility in water partly because of their differing polarities. This insolubility seriously hinders the degradation of these materials because water is often an important element for promoting faster degradation (e.g., by hydrolysis) and only the outer surface of insoluble materials is in contact with water.

Being insoluble in water causes particular difficulties to biodegradation of these materials because the predominant majority of microorganisms can uptake only small soluble organics. For larger molecules, even if water soluble, the microorganisms need to produce and release specific enzymes into the surrounding water to break these larger molecules into smaller, ingestible molecules. Producing enzymes requires valuable resources of microorganisms. It is also difficult to minimize or prevent consumption of the enzyme-generated smaller organics by other neighboring microorganisms. The situation is even worse for insoluble material because these degradation enzymes can lose their functions by being adsorbed onto other components. Phagotrophic algae can engulf these insoluble materials and digest them with special enzymes that they keep inside their bodies without sharing the food generated with others.

In one or more embodiments, the algae are preferably of the *Ochromonas danica* microalgae species. Microalgae

*Ochromonas danica* (*O. danica*) are commonly in a teardrop or spherical shape and have two unequal flagellates and one chloroplast. The alga can grow on soluble organics (heterotrophy) and by photosynthesis. It can also grow phagotrophically by engulfing oil droplets, particles, and bacteria. This alga can also grow on substrates such as starch grains, casein, small organisms, phenols, phenolic mixtures, fats, alcohols, carboxylic acids and amino acids.

For at least the *O. danica* algae species, evidence suggests that the engulfment of food particles by these cells is facilitated by the movement of their flagellates. For this and other alga species, cell hydrophobicity is also a factor that promotes the alga's phagotrophic ingestion of oil droplets, by increasing the contact affinity and attachment of the algal cells to oil droplets. In general, the more hydrophobic the algae cells, the better the attachment to oil droplets when the oil floats to an upper phase. Evidence suggests that mixing a medium allows the algae cells to attach to oil droplets. Then, when mixing is ceased, the oil droplets move to the upper phase since they are not soluble with water. Thus, since higher hydrophobicity generally gives more attachment of the algae to the oil droplets, higher hydrophobic cell surface provides improved recovery of the algae following this movement or flotation.

The ability of the algae cells to attach to oil droplets can be measured using optical density calculations. Optical density can be measured directly by spectrophotometry (e.g. Spectronic 20, Thermo Electron Corporation, Waltham, Mass.). The optical density (OD) is measured at a predetermined distance. In one or more embodiments, this predetermined distance is 400 nm ($OD_{400}$) or approximate thereto. Then the initial OD and final OD are measured to determine the effectiveness of the partitioning of the cells to the interface. The percentage of cells partitioned can be calculated as $$\left(1 - \frac{OD_{final}}{OD_{initial}}\right) \times 100.$$

This calculation then gives an approximation of the percentage of algae cells that are removed from the aqueous phase to the oil-water interface. In one or more embodiments, this percentage is from 63 percent or more to 79 percent or less. In one or more embodiments, this percentage is 71 percent or approximate thereto. In one or more embodiments, this percentage is 63 percent or more.

Other suitable phagotrophic algae may be chosen from several chrysomonad genera including *Dinobryon*, *Chrysophaerella*, *Uroglena*, *Catenochrysis*, *Ochromonas*, *Chromulina*, and *Chrysococcus*; the prymnesiophyte *Chrysochromulina*; the coccolithophorid *Coccolithus pelagicus*; the xanthophyte *Chlorochromonas*, the chrysophytes *Phaeaster*, *Chrysamoeba*, and *Pedinella*; the dinoflagellate *Ceratium hirundinella* Muller; and *Cryptomonas ovata* Ehrenberg.

In one or more embodiments, the algae are selected from *Chlorella* and *Ochromonas* species. In one or more embodiments, the algae are *Ochromonas* species. In one or more embodiments, the algae are *Chlorella* species.

Other suitable phagotrophic may be chosen from *Dinobryon* chrysomonads, *Chrysophaerella* chrysomonads, *Uroglena* chrysomonads, *Catenochrysis* chrysomonads, *Ochromonas* chrysomonads, *Chromulina* chrysomonads, *Chrysococcus* chrysomonads, *Chrysochromulina* prymnesiophytes, *Coccolithus pelagicus* coccolithophorids, *Chlorochromonas* xanthophytes, *Phaeaster* chrysophytes, *Chrysamoeba* chrysophytes, *Pedinella* chrysophytes, *Ceratium* hirundinella, and *Cryptomonas* ovate.

Still other suitable phagotrophic may be chosen from *Ochromonas* species including *Ochromonas malhamensis*, *Ochromonas tuberculata*, *Ochromonas vallescia*, and other *Ochromonas* chrysophytes.

As discussed above, the algae are preferably phagotrophic, but can also be described by other classifications. Photosynthetic are those algae that utilize light as their energy source through the process of photosynthesis. Heterotrophic algae are those that feed on organic substrates.

Osmotrophic algae uptake dissolved compounds through a membrane via osmosis or other active transport mechanisms (excluding phagotrophy) across the membrane. Suitable osmotrophic algae may be chosen from *Achnanthes orientalis*, *Agmenellum*, *Amphiprora hyaline*, *Amphora coffeiformis*, *Amphora coffeiformis linea*, *Amphora coffeiformis punctata*, *Amphora coffeiformis taylori*, *Amphora coffeiformis tenuis*, *Amphora delicatissima*, *Amphora delicatissima capitata*, *Amphora* sp., *Anabaena*, *Ankistrodesmus*, *Ankistrodesmus falcatus*, *Boekelovia hooglandii*, *Borodinella* sp., *Botryococcus braunii*, *Botryococcus sudeticus*, *Carteria*, *Chaetoceros gracilis*, *Chaetoceros muelleri*, *Chaetoceros muelleri subsalsum*, *Chaetoceros* sp., *Chlorella anitrata*, *Chlorella Antarctica*, *Chlorella aureoviridis*, *Chlorella candida*, *Chlorella capsulate*, *Chlorella desiccate*, *Chlorella ellipsoidea*, *Chlorella emersonii*, *Chlorella fusca*, *Chlorella fusca* var. *vacuolata*, *Chlorella glucotropha*, *Chlorella infusionum*, *Chlorella infusionum* var. *actophila*, *Chlorella infusionum* var. *auxenophila*, *Chlorella kessleri*, *Chlorella lobophora*, *Chlorella luteoviridis*, *Chlorella luteoviridis* var. *aureoviridis*, *Chlorella luteoviridis* var. *lutescens*, *Chlorella miniata*, *Chlorella minutissima*, *Chlorella mutabilis*, *Chlorella nocturna*, *Chlorella parva*, *Chlorella photophila*, *Chlorella pringsheimii*, *Chlorella Protothecoides*, *Chlorella protothecoides* var. *acidicola*, *Chlorella regularis*, *Chlorella regularis* var. *minima*, *Chlorella regularis* var. *umbricata*, *Chlorella reisiglii*, *Chlorella saccharophila*, *Chlorella saccharophila* var. *ellipsoidea*, *Chlorella salina*, *Chlorella simplex*, *Chlorella sorokiniana*, *Chlorella* sp., *Chlorella sphaerica*, *Chlorella stigmatophora*, *Chlorella vanniellii*, *Chlorella vulgaris*, *Chlorella vulgaris*, *Chlorella vulgaris f. tertia*, *Chlorella vulgaris* var. *autotrophica*, *Chlorella vulgaris* var. *viridis*, *Chlorella vulgaris* var. *vulgaris*, *Chlorella vulgaris* var. *vulgaris f. tertia*, *Chlorella vulgaris* var. *vulgaris f. viridis*, *Chlorella xanthella*, *Chlorella zofingiensis*, *Chlorella trebouxioides*, *Chlorella vulgaris*, *Chlorococcum infusionum*, *Chlorococcum* sp., *Chlorogonium*, *Chroomonas* sp., *Chrysosphaera* sp., *Cricosphaera* sp., *Cryptomonas* sp., *Cyclotella cryptica*, *Cyclotella meneghiniana*, *Cyclotella* sp., *Dunaliella* sp., *Dunaliella bardawil*, *Dunaliella bioculata*, *Dunaliella granulate*, *Dunaliella maritime*, *Dunaliella minuta*, *Dunaliella parva*, *Dunaliella peircei*, *Dunaliella primolecta*, *Dunaliella salina*, *Dunaliella terricola*, *Dunaliella tertiolecta*, *Dunaliella viridis*, *Dunaliella tertiolecta*, *Eremosphaera viridis*, *Eremosphaera* sp., *Ellipsoidon* sp., *Euglena*, *Franceia* sp., *Fragilaria crotonensis*, *Fragilaria* sp., *Gleocapsa* sp., *Gloeothamnion* sp., *Hymenomonas* sp., *Isochrysis aff. galbana*, *Isochrysis galbana*, *Lepocinclis*, *Micractinium*, *Micractinium*, *Monoraphidium minutum*, *Monoraphidium* sp., *Nannochloris* sp., *Nannochloropsis salina*, *Nannochloropsis* sp., *Navicula acceptata*, *Navicula biskanterae*, *Navicula pseudotenelloides*, *Navicula pelliculosa*, *Navicula saprophila*, *Navicula* sp., *Nephrochloris* sp., *Nephroselmis* sp., *Nitschia communis*, *Nitzschia alexandrina*, *Nitzschia communis*, *Nitzschia dissipata*, *Nitzschia*

*frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Pascheria acidophila, Pavlova* sp., *Phagus, Phormidium, Platymonas* sp., *Pleurochrysis carterae, Pleurochrysis dentate, Pleurochrysis* sp., *Prototheca wickerhamii, Prototheca stagnora, Prototheca portoricensis, Prototheca moriformis, Prototheca zopfii, Pyramimonas* sp., *Pyrobotrys, Sarcinoid chrysophyte, Scenedesmus armatus, Spirogyra, Spirulina platensis, Stichococcus* sp., *Synechococcus* sp., *Tetraedron, Tetraselmis* sp., *Tetraselmis suecica, Thalassiosira weissflogii,* and *Viridiella fridericiana.*

A wide range of useful algae products can be developed from algae and the algal components and byproducts once the algae has engulfed and processed the oil or grease. Examples of algal products include algal biomass, dry algal cells, algal proteins, algal lipids, and algal carbohydrates. Algal biomass and algal lipid can be further converted into biofuel. Other examples of algal products include specialty substances with nutritional, pharmaceutical, cosmetic, and industrial uses.

Biomass can be generally described as biological material derived from living, or recently living organisms. With respect to algal biomass, it can be described as the wet algal cell mass separated from the aqueous medium in which the algal cells are cultivated or as the totally or partially dried algal cell mass. Biomass can be used as an energy source directly via combustion or co-combustion with other fuel to produce heat, or indirectly after converting the biomass to biofuel.

Biofuel can be generally described as fuel that contains energy from geologically recent carbon fixation. Here, biofuel is fuel that is produced from the algae and algae products. Biomass can be converted to biofuel and other energy containing substances in three different ways: thermal conversion, chemical conversion, and biochemical conversion.

Lipids may be broadly defined as hydrophobic or amphiphilic small molecules. The main biological functions of lipids include storing energy, signaling, and acting as structural components of cell membranes. Lipids can be particularly converted to biofuel by extracting the lipids and reacting them with alcohols, such as methanol or ethanol, through well-known chemical or enzymatic processes to make biodiesel, i.e., methyl or ethyl esters of fatty acids.

The conditions, such as time, pH, temperature, and dissolved oxygen, of the algae and the combined mixture of the algae and the oil-containing medium can be adjusted to any conditions that will physiologically support the algae.

The algae and the oil-containing medium are combined for a period of time that can be selected based on the particular algae and oil-containing medium that are utilized. In one or more embodiments, this timeframe is from 1 hour or more to 5 days or less. In one or more embodiments, this timeframe is from 3 hours or more to 3 days or less. In one or more embodiments, this timeframe is 1 hour or approximate thereto. In one or more embodiments, this timeframe is 3 hours or approximate thereto.

The pH of the algae and combined mixture should be maintained within the physiologically acceptable range for the algae. The pH can also affect the transport/uptake of solid organic materials by algae. The pH can be controlled by any means known in the art. In one or more embodiments, the pH is from 2.5 or more to 8.5 or less. In one or more embodiments, the pH is from 4.0 or more to 6.0 or less.

The temperature of the algae and combined mixture should be maintained within the physiologically acceptable range for the algae. The temperature can be controlled by any heating or cooling equipment as known in the art. Such equipment may employ temperature sensors, thermometers, thermocouples and the like to monitor temperature, further including heating and/or cooling elements to control the temperature of the medium as monitored by those elements. Cooling is normally achieved by running cold water or other fluids through tubes or plates that are in contact with the algae and combined mixture. Heating is often achieved either by running hot water or other fluids through tubes or plates that are in contact with the algae and combined mixture, or by using electrically heated tubes, plates or other surfaces.

In one or more embodiments, the algae and combined mixture are maintained at from 10° C. or more to 40° C. or less, in other embodiments, from 13° C. or more to 35° C. or less, and in still other embodiments, from 15° C. or more to 30° C. or less. In one or more embodiments, the algae and combined mixture are at a temperature of 18° C. or more. In one or more embodiments, the algae and combined mixture are at a temperature of 28° C. or less. It should be noted that different algae have different physiologically suitable and tolerable temperatures. The optimal temperatures may be adjusted if more thermophilic or more psychrophilic algae are used.

The dissolved oxygen content of the algae and combined mixture should be maintained within the physiologically acceptable range for the algae. The dissolved oxygen content can be controlled by any means known in the art. In one or more embodiments, the dissolved oxygen content of the algae and combined mixture is controlled by adjusting the aeration flow rate and/or oxygen partial pressure of the gas (air, pure oxygen or mixtures of air and oxygen) and/or by adjusting the speed of mechanical agitation. The aeration rate and agitation speed are maintained within the range that provides adequate mixing without damaging or killing the algae cells (due to high shear stress or other damaging mechanisms).

In one or more embodiments, the algae and combined mixture have a dissolved oxygen content of from 0.02 milligram per liter (mg/L) or more to 10 mg/L or less, in other embodiments, from 0.05 mg/L or more to 5 mg/L or less, and in still other embodiments, from 0.1 mg/L or more to 2 mg/L or less. In one or more embodiments, the algae and combined mixture have a dissolved oxygen content of 0.2 mg/L or more. In one or more embodiments, the algae and combined mixture have a dissolved oxygen content of 1.5 mg/L or less.

The size of the oil droplets can affect the ability of the algae to engulf the oil. In general, the smaller the oil droplet size, the easier it is for the algae to engulf the oil. A smaller oil size can also lead to increased population growth, both faster growth and larger number of total cells, of the algae. However, where float procedures are used to float the oil at the top of an oil-containing medium, the smaller oil droplets take longer to float to the top of the medium. The reverse is also true, that larger oil droplets generally move faster to the top of the medium. In one or more embodiments, known methods of making droplets smaller are utilized. Such methods can include agitation or mixing.

In one or more embodiments, the presence of surface-active components or impurities in the oil-containing medium enhances the formation of finer droplets, which are easier to engulf by the alga. The oil-containing medium of waste cooking oil (WCO) is one example of a medium that includes surface-active components or impurities.

In one or more embodiments, where larger oil droplets are present, a surfactant can be added to an oil-containing medium to help with the dispersion of the oil droplets. When olive oil is an oil in an oil-containing medium, the oil droplets are large and therefore they can particularly benefit from the addition of a surfactant. One example of a suitable surfactant is a surfactant that is a nonionic surfactant and an emulsifier. A surfactant can be derived from polyethoxylated sorbitan and oleic acid. A particularly useful surfactant is Tween® 80, known by the chemical names of polysorbate 80, polyoxyethylene (20) sorbitan monooleate, or (x)-sorbitan mono-9-octadecenoate poly(oxy-1,2-ethanediyl). In one or more embodiments, the amount of surfactant added is from 0.01 g/L or more to 0.20 g/L or less, in other embodiments from 0.05 g/L or more to 0.10 g/L or less, and in other embodiments 0.08 g/L, or approximate thereto, based on the total volume of the medium. In one or more embodiments, the addition of a surfactant and the subsequent improved dispersion can reduce the time that it takes for the algae cell population to double. In one or more embodiments, the algae cell population doubling time is decreased from 15.3±0.2 h to 13.2±0.6 h, based on the addition of a surfactant.

Where larger oil droplets are present, the large intracellular oil droplets are seen at the early cultivation stage in the oil-containing medium, but the droplets become smaller towards the end of cultivation. Without being limited to any theory, this reduction in size is based on either the engulfed larger oil droplets being gradually consumed into smaller droplets or the larger oil droplets being broken down to small droplets to facilitate digestion or storage. Some of the algae cells may have one or two larger oil droplets inside, while other cells may have multiple small droplets.

The percent treatment or percent treatment completion is a measure of how effective the algae are at treating the oil present in an oil-containing medium. Depending on the complexity of an oil composition, the sensitivity of available methods for measuring the amounts of residual oil, and the availability of standards to perform calibration for all oil components by, for example, the liquid chromatography-based detection methods, different equations are used to calculate the percent treatment completion. Two examples of equations to determine percent treatment completion are shown below.

Percent treatment completion=[(Initial oil concentration at the beginning of cultivation−oil concentration at the end of cultivation)/(Initial oil concentration at the beginning of cultivation)]×100    Equation 1:

Percent treatment completion=[(Total peak area in sample taken at the beginning of cultivation−total peak area in sample taken at the end of cultivation)/(Total peak area in initial sample)]×100    Equation 2:

Equation 1 can be used for embodiments when the oil has only a few components and analytical standards and calibration equations can be developed for all these components to quantify the concentration of each component and sum them together for the total oil concentration. Equation 1 can also be used for embodiments when the oil concentration is high enough so that by, for example, solvent extraction, a sufficient amount of oil can be collected and accurately weighed to give the total oil concentration. Equation 2 can be used for embodiments when a suitable liquid or gas chromatography-based analytical method coupled with a suitable detection method, for example, by a UV detector or a mass spectrometer, is used to generate a chromatogram for the sample analyzed but the standards or calibration equations are not available for all oil components in the sample. The oil concentration is the concentration of oil in an oil-containing medium. The beginning and end of cultivation are the moments when the algae are brought into contact with the oil-containing medium and when the treatment process or experiment ends, respectively. Using gas chromatography or high-performance liquid chromatography equipment, a peak area is a measurement obtained by integration of the changing chromatogram peak height over an interval during which a component of the composition is coming out of the chromatographic column and the peak area thus obtained reflects the concentration of that component. A summation of all peak areas, or the total peak area, reflects an estimation of the total oil concentration. Equation 2 can therefore be used to approximate the percentage of oil removal.

In one or more embodiments, the percent treatment is 40 percent or more, in other embodiments 50 percent or more, in other embodiments 53.8 percent or more, in other embodiments 80.5 percent or more, in other embodiments 85 percent or more, in other embodiments 88 percent or more, and in other embodiments 95 percent or more.

The oil concentration is the concentration of oil in an oil-containing medium and can be given in g/L units. It is representative of the amount of oil present in an oil-containing medium. The algae serve to reduce the oil concentration of the medium, by engulfing the oil, when comparing the initial concentration and the concentration after a predetermined time. The final oil concentration is also less than the initial oil concentration.

In one or more embodiments, the oil concentration is reduced from 12.8 g/L or more to 5.9 g/L or less, in other embodiments the oil concentration is reduced from 10 g/L or more to 2 g/L or less, and in other embodiments the oil concentration is reduced from 1.73 g/L or more to 0.06 g/L or less.

In one or more embodiments, the oil concentration is reduced by 50 percent or more, in other embodiments the oil concentration is reduced by 80 percent or more, and in other embodiments the oil concentration is reduced by 96 percent or more.

The specific growth rate ($\mu(h^{-1})$) of the algae is a measure of how quickly the algae grow. It can be determined using the slope of a semi-logarithmic plot of cell concentration (g/L), versus cultivation time (hours). The algae can be characterized by a maximum specific growth rate ($\mu_{max}$), which is the highest growth rate and typically occurs during a period of exponential increase of cell population. The maximum specific growth rate is observed in the complete batch process of cultivation. The $\mu_{max}$ value differs according to species, temperature, pH, dissolved oxygen, and detailed medium composition. In one or more embodiments, the algae have $\mu_{max}$ values in range of from 0.029 to 0.23 (1/h) depending on the cultivation conditions.

In one or more embodiments, the algae have a $\mu_{max}$ value of 0.047 (1/h) or approximate thereto, in other embodiments 0.052 (1/h) or approximate thereto, in other embodiments 0.080 (1/h) or approximate thereto, and in other embodiments 0.090 (1/h) or approximate thereto.

The cell number concentration of the algae is a measure of the amount of algae cells that are present per volume of medium. It can be given with the unit of number of cells per mL. Cell number concentration can be determined by a counting chamber, such as the counter provided by Petroff- Hausser (C. A. Hausser and Son, Philadelphia, Pa.). The sample of algae cells can be fixed with an equal volume of 2% glutaraldehyde and then counted under a light microscope (Olympus) coupled with a digital camera (DP71; Olympus America). The algae can be characterized by a maximum cell number concentration (Xmax), which is the maximum concentration reached in a cultivation process, depending on the concentrations of all nutrients essential for growth, the concentrations of potential toxic or inhibitory compounds, and the physical and chemical conditions of the process.

In one or more embodiments, a medium has a maximum cell number concentration of $2.8 \times 10^7$ cells/mL or more and in other embodiments $1.7 \times 10^7$ cells/mL or more. In one or more embodiments, a medium has a maximum cell number concentration of $2.89 \times 10^7$ cells/mL or approximate thereto, and in other embodiments $1.77 \times 10^7$ cells/mL or approximate thereto.

In one or more embodiments, steps of depleting at least one soluble nutrient component essential for microbial growth can be utilized. Such depletion steps are further disclosed in co-pending application U.S. Application Publication 2014/0038247, which is incorporated herein by reference.

In embodiments utilizing a process, the process can be any process that combines suitable algae with an oil-containing medium. The algae can be introduced to the oil-containing medium or the oil-containing medium can be introduced to the algae. Other suitable methods include filtration methods through a column.

One or more embodiments of the present invention involve a method comprising one or more of the following steps: providing an algae, providing a mineral medium, growing an algae within a mineral medium, providing an oil-containing medium, combining an algae with an oil-containing medium, allowing the algae to engulf or uptake at least a portion of the oil in the oil-containing medium and thereby process the oil, allowing the algae to grow by engulfing or uptaking at least a portion of the oil in the oil-containing medium, collecting the algae, producing an algal product, and depleting at least one soluble nutrient component essential for microbial growth.

The present invention provides one or more of the following advantages: allowing the use of less expensive biodiesel feedstocks, ability to treat oil and/or grease in water and wastewater, ability to treat microdispersed oil, more economic production of biodiesel, and improved properties of a resulting product such as biodiesel.

EXAMPLES

Example 1

As one example for demonstrating the present invention, microalga (*Ochromonas danica*) seed culture was grown in four 500 mL Erlenmeyer flasks. The mineral medium used contained 0.2 g/L nitrilotriacetic acid, 0.3 g/L $KH_2PO_4$, 0.4 g/L $MgCO_3$, 0.05 g/L $CaCO_3$, 0.24 g/L $NH_4Cl$, 0.1 g/L $MgSO_4 \cdot 7H_2O$, 10 g/L glucose, 0.5 g/L peptone, 0.5 g/L yeast extract, 4.4 mg/L $Na_2EDTA$, 3.15 mg/L $FeCl_3 \cdot 6H_2O$, 0.97 mg/L $H_3BO_3$, 0.25 mg/L thiamine, 0.18 mg/L $MnCl_2 \cdot 4H_2O$, 0.02 mg/L $ZnSO_4 \cdot 7H_2O$, 0.01 mg/L $CoCl_2 \cdot 6H_2O$, 6 µg/L $Na_2MoO_4 \cdot 2H_2O$ and 2.5 µg/L biotin. Mixing was provided by a magnetic stir bar at 250 rpm. Algae cells were grown at room temperature (22±1° C.) and the ambient light. The initial pH of the algae medium was adjusted to 7 by addition of 0.05 N NaOH. Algae cells grown to the late growth phase or early stationary phase were used as the inocula for this example.

Four tests were done, each with 100 mL mineral medium described above (without glucose in two of the systems) in a 500 mL flask. In three tests the mineral medium was added with simulated oily wastewaters taken from a pretreatment process of high free fatty acid (FFA) oils, and the algae growth in these oil-containing mediums was compared with that in the mineral medium without oily wastewater (the control). The oil pretreatment process forms a FFA-rich middle phase between the upper oil phase with much reduced FFA content and the bottom aqueous phase with residual concentrations of dissolved and dispersed oil and FFA components.

For System 1 the 100 mL mineral medium was added with 1 mL of the FFA-rich middle phase (an unspecified volume of the bottom aqueous phase was inevitably taken in the total 1 mL oily wastewater added). System 2 was similar to System 1 with the exception that no glucose was added in the mineral medium used. Glucose was also not added in the mineral medium for System 3. In addition, the 1 mL oily wastewater added for System 3 was taken from the bottom aqueous phase, without the FFA-rich middle phase. System 4 was the oil/FFA-free control system and included the above algae mineral medium with 10 g/L glucose. The glucose and the emulsified oils, dissolved oils, and some unspecified substances introduced with the pretreated high FFA waste oils served as carbon sources for *O. danica* growth. Experiments were done batch-wise using stir plates, stirring bars, and Erlenmeyer flasks.

A modified Bligh extraction procedure using chloroform-methanol in a 2:1 volumetric ratio was used to measure the percent completion of treatment, by following the actual weight of oil remaining, i.e. not processed by the algae, in the resulting medium following the algal treatment. 2 mL samples were taken from each system at different incremental times. The samples were centrifuged at 300 g for 15 minutes to separate the algae cells, as a pellet gathered at the bottom of centrifuge tube, from the supernatant that contained dissolved and suspended oil droplets. The supernatant was collected and saved for extraction with the chloroform-methanol solvent.

For extraction, 10 mL of chloroform-methanol (2:1, v/v) was added to the samples. Then, 2 drops of concentrated hydrochloric acid (5 N) was also added. The mixture was next vortexed for 10 minutes and centrifuged at 300 g for 15 minutes. The majority of the upper aqueous layer was gently removed and discarded. 1 mL deionized water and 2 drops of concentrated hydrochloric acid (5 N) were added to the remaining solvent mixture, which was then centrifuged again at 300 g for 15 minutes. The lower chloroform layer containing the extracted oil was next collected into a pre-weighed drying vessel. 5 mL of chloroform was again added to the centrifuge tube, vortexed 30 seconds, and centrifuged at 300 g for 15 minutes. The lower chloroform layer was again added into the pre-weighed drying vessel (the same one from previous step). The organic extract was dried under a stream of nitrogen at room temperature to a constant weight. The percent completion of treatment, or oil removal, by the microalga for each oily wastewater sample was then calculated according to the following equation:

Percent treatment completion=[(Initial oil concentration at the beginning of cultivation−oil concentration at the end of cultivation)/(Initial oil concentration at the beginning of cultivation)]×100.

Because the amounts of oil were very low, particularly for System 3 and for all samples after algal treatment, there might be concerns over the accuracy of extraction method used above. Separate analysis was also carried out using Hewlett Packard series 1100 high-performance liquid chromatography (HPLC) equipment. The samples were separated using a Supelcosil LC-18 column (4.6 mm×250 mm, 5 µm) at ambient temperature. The samples were first dissolved in 1 mL 50% acetonitrile and 50% water then filtered using PVDF filter. The mobile phase was a mixture of acetonitrile and water, used in the following gradient scheme: 0-3 min, held at 50% acetonitrile, 50% water; 3-43 min, increased gradually to 95% acetonitrile, 5% water; 43-53 min, held at 95% acetonitrile, 5% water; 53-60 min, decreased slowly back to 50% acetonitrile, 50% water; 60-65 min, held at 50% acetonitrile, 50% water. The flow rate was 0.4 mL/min and the injection volume was 20 µL. The oil concentration in sample was assumed to be proportional to the total peak area in the chromatogram. The percent treatment completion was then estimated according to the following equation:

Percent treatment completion=[(Total peak area in sample taken at the beginning of cultivation−total peak area in sample taken at the end of cultivation)/(Total peak area in initial sample)]×100.

The following properties for Systems 1 through 4 are summarized in Table 1: the maximum specific growth rates ($\mu max$; 1/h), the maximum cell number concentration reached (Xmax), the average cell sizes (volume) of final samples ($\mu m^3$), and the average percent treatment completion of oily wastewaters. The cell number concentrations were plotted against time in semi-logarithmic plots. The data points in the linear regime (representing the exponential-growth phase) were fitted to obtain the maximum specific growth rate $\mu max$ (1/h).

$\mu max$ ($h^{-1}$) of 0.052. This growth rate was similar to that in System 3 but slower than the growth in the other two systems.

The highest cell number concentration, i.e., (2.89±0.08)×$10^7$ cells/mL, was also achieved in System 1. The glucose-based medium (System 4) supported a maximum cell number concentration of (1.77±0.06)×$10^7$ cells/mL.

As given in Table 1, the cells grown in Systems 1-3 were similar in sizes and were greater than 20 percent larger than the cells grown in System 4 (230±4 $\mu m^3$). Evidence suggests that the algal cells grown on oil were larger than the cells on glucose alone because of expansion due to the engulfed oil droplets. The cells grown in Systems 1-3 were observed to have multiple intracellular oil droplets, which were likely responsible for the expanded cell size. The largest cell size of 287±5 $\mu m^3$ was found in System 2.

Close examination of captured microscopic pictures showed that the algal cells could engulf complex oil droplets with the individual droplet volumes up to 10 $\mu m^3$, or approximate thereto. Cells were also observed to have multiple small oil droplets with volumes ranging from 1 $\mu m^3$ to 3 $\mu m^3$. A correlation was made for the results of the overall treatment yield by extraction versus the yield of total area reduction for all picks in each oily wastewater system by HPLC analysis. The linear equation (y=0.0731 x+81.249) fitted with $R^2$=0.899, shows an acceptable correlation of the results from the two methods.

The actual concentration of oil extracted at three cultivation times (beginning of cultivation, late-exponential phase, and final cultivation time of microalga) and the treatment yield measured by the chloroform-methanol extraction method for Systems 1-3 were as follows: System 1 was reduced from 12.8 g/L to 5.94 g/L, a 53.8% reduction, over 150 h of cultivation; in System 2, the oil concentration was

TABLE 1

Properties of Systems 1 through 4

| System | Initial oil (g/l) | Initial glucose (g/L) | $\mu_{max}$ ($h^{-1}$) | Cell volume ($\mu m^3$) | Max cell number ($10^7$ cells/ml) | Treatment yield (%) by extraction | Treatment yield (%) by HPLC analysis |
|---|---|---|---|---|---|---|---|
| 1 | 12.8 | 10 | 0.080 | 280 ± 4 | 2.89 ± 0.08 | 53.8 | 85 |
| 2 | 10.04 | 0 | 0.090 | 287 ± 5 | 2.83 ± 0.05 | 80.5 | 87.7 |
| 3 | 1.73 | 0 | 0.047 | 278 ± 5 | 172 ± 0.03 | 96.7 | 88 |
| 4 | 0 | 10 | 0.052 | 230 ± 4 | 1.77 ± 0.06 | N/A | N/A |

System 3 that had only the bottom aqueous phase without the FFA-rich middle phase had an initial oil concentration of 1.73 g/L. The two other oil-containing water systems (1 and 2) had initial oil concentrations of 12.8 and 10.0 g/L, respectively. The higher oil concentrations for these systems were due to these systems containing the oily materials that accumulated at the oil-water interface resulting from the FFA pretreatment process.

The higher $\mu max$ ($h^{-1}$), 0.080 and 0.090, were observed when the alga was grown in the two systems with higher oil concentrations. Evidence suggests that the faster growth was also promoted by the presence of more free fatty acids (FFAs), which were more soluble or dispersible than glycerides. It is also believed that FFAs complexed with Ca or Fe ions accumulated in the middle phase in the FFA pretreatment process, because of their surface-active properties, limited solubility in either oil or aqueous phases, and densities. The cell growth in the glucose-based medium had a reduced from 10.04 g/L to 1.96 g/L, a 80.5% reduction, and in System 3 with 1.73 g/L initial oil, the reduction was 96.7%. The treatment yield based on the total peak area for each sample obtained by HPLC method were 85%, 87.7%, and 88%, respectively.

In light of the foregoing, it should be appreciated that the present invention significantly advances the art by providing an improved method and system of treating water having oils and greases therein. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A method for treating an industrial wastewater medium, the method comprising steps of:

providing a wastewater stream including industrial wastewater and at least one of oil or grease, the at least one of oil or grease being in the form of droplets having an initial droplet size, wherein at least a portion of the at least one of oil or grease is insoluble in the industrial wastewater, combining phagotrophic algae with the wastewater stream to form a combined medium, wherein the combined medium has a maximum cell number concentration of the phagotrophic algae of $2.89 \times 10^7$ algae cells/mL of the combined medium, wherein the phagotrophic algae are selected from the group consisting of *Dinobryon, Chrysophaerella, Uroglena, Catenochrysis, Chromulina*, and *Chrysococcus,* mechanically agitating or mechanically mixing the combined medium to thereby form the droplets into a smaller droplet size smaller than the initial droplet size, and allowing the algae to engulf at least a portion of the insoluble portion in the combined medium, wherein the wastewater stream has an oil concentration of 12.8 g/L or more prior to the step of combining and the combined medium has an oil concentration of 5.9 g/L or less after the step of allowing.

2. The method of claim 1, wherein the wastewater stream further includes a mineral medium, and wherein the method further includes a step of growing the phagotrophic algae within the combined medium, wherein the mineral medium comprises one or more of nitrilotriacetic acid, $KH_2PO_4$, $MgCO_3$, $CaCO_3$, $NH_4Cl$, $MgSO_4.7H_2O$, yeast extract, peptone, $Na_2EDTA$, $FeCl_3.6H_2O$, $H_3BO_3$, thiamine, biotin, $MnCl_2.4H_2O$, $ZnSO_4.7H_2O$, $CoCl_2.6H_2O$, and $Na_2MoO_4.2H_2O$.

3. A method for treating an industrial wastewater medium, the method comprising steps of:
providing a wastewater stream including industrial wastewater and at least one of oil or grease, the at least one of oil or grease being in the form of droplets having an initial droplet size, wherein at least a portion of the at least one of oil or grease is insoluble in the industrial wastewater, combining phagotrophic algae with the wastewater stream to form a combined medium, wherein the combined medium has a maximum cell number concentration of the phagotrophic algae of $2.89 \times 10^7$ algae cells/mL of the combined medium, wherein the phagotrophic algae are selected from *Ochromonas danica, Ochromonas malhamensis, Ochromonas tuberculata*, and *Ochromonas vallescia,* mechanically agitating or mechanically mixing the combined medium to thereby form the droplets into a smaller droplet size smaller than the initial droplet size, and allowing the algae to engulf at least a portion of the insoluble portion in the combined medium, wherein the wastewater stream has an oil concentration of 12.8 g/L or more prior to the step of combining and the combined medium has an oil concentration of 5.9 g/L or less after the step of allowing.

4. The method of claim 1, further comprising steps of collecting the algae and producing an algal product, following the step of allowing.

5. The method of claim 1, wherein the wastewater stream comprises waste cooking oil.

6. The method of claim 1, further comprising steps of depleting at least one soluble nutrient component essential for microbial growth, and allowing, after the step of depleting, the phagotrophic algae to grow as the predominant algae.

7. A method for treating an industrial wastewater medium, the method comprising steps of:
combining phagotrophic algae with a wastewater medium including industrial wastewater and at least one of oil or grease to form a combined medium, the at least one of oil or grease being in the form of droplets having a droplet size, wherein at least a portion of the at least one of oil or grease in the combined medium is insoluble in the industrial water, wherein the combined medium has a maximum cell number concentration of the phagotrophic algae of $2.89 \times 10^7$ algae cells/mL of the combined medium, wherein the phagotrophic algae are selected from the group consisting of *Dinobryon, Chrysophaerella, Uroglena, Catenochrysis, Chromulina*, and *Chrysococcus,* adding a surfactant to the combined medium, wherein the surfactant functions as both a nonionic surfactant and an emulsifier, wherein the amount of the surfactant added is from 0.01 g/L or more to 0.20 g/L or less, based on the total volume of the combined medium, mechanically agitating or mechanically mixing the combined medium to thereby form the droplets into a smaller droplet size smaller than the initial droplet size, and allowing the algae to engulf at least a portion of the insoluble portion in the combined medium, wherein the wastewater medium has an oil concentration of 10 g/L or more prior to the step of combining and the combined medium has an oil concentration of 2 g/L or less after the step of allowing.

8. The method of claim 1, wherein the steps of combining and allowing occur at a dissolved oxygen content of from 0.05 mg/L or more to 5 mg/L or less and at a pH of from 4.0 or more to 6.0 or less.

9. The method of claim 1, wherein the wastewater stream includes both of oil and grease.

10. The method of claim 1, wherein the method occurs within a timeframe of from 3 hours or more to 3 days or less.

11. The method of claim 7, wherein the method occurs within a timeframe of from 3 hours or more to 3 days or less.

12. The method of claim 7, wherein the amount of surfactant added is from 0.05 g/L or more to 0.10 g/L or less, based on the total volume of the combined medium.

13. The method of claim 12, wherein the surfactant is polysorbate 80.

14. The method of claim 1, wherein the combined medium includes the at least one of oil or grease as a sole carbon source for growth of the phagotrophic algae.

15. The method of claim 1, wherein the step of providing includes providing the wastewater stream from a chemical plant or an oil refinery.

16. The method of claim 1, wherein the method occurs within a timeframe of about 1 hour.

17. The method of claim 1, wherein the method occurs within a timeframe of about 3 hours.

18. The method of claim 1, wherein the step of mechanically agitating or mechanically mixing utilizes a magnetic stir bar.

19. The method of claim 1, wherein the combined medium includes an upper oil-containing phase and a lower aqueous phase, wherein, during the step of allowing, the droplets and a percentage of the phagotrophic algae float to the upper oil-containing phase, and wherein, after the step of allowing, the percentage of phagotrophic algae floated to the upper oil-containing phase is from 63 percent or more to 79 percent or less, as determined by optical density.

20. The method of claim 2, wherein, during the step of growing the phagotrophic algae, the phagotrophic algae have a maximum specific growth rate ($\mu_{max}$) of from 0.029 $h^{-1}$ to 0.23 $h^{-1}$, as determined by the slope of a semi-logarithmic plot of cell concentration (g/L) versus cultivation time (hours).

* * * * *